US012630500B2

(12) United States Patent
Bejger

(10) Patent No.: US 12,630,500 B2
(45) Date of Patent: May 19, 2026

(54) HEXASUBSTITUTED RADIALENE COMPOUNDS AND APPLICATIONS THEREOF

(71) Applicant: THE UNIVERSITY OF NORTH CAROLINA AT CHARLOTTE, Charlotte, NC (US)

(72) Inventor: Christopher Bejger, Charlotte, NC (US)

(73) Assignee: THE UNIVERSITY OF NORTH CAROLINA AT CHARLOTTE NC, Charlotte, NC (US)

( * ) Notice: Subject to any disclaimer, the term of this patent is extended or adjusted under 35 U.S.C. 154(b) by 511 days.

(21) Appl. No.: 18/106,713

(22) Filed: Feb. 7, 2023

(65) Prior Publication Data

US 2023/0174466 A1 Jun. 8, 2023

Related U.S. Application Data

(63) Continuation-in-part of application No. 17/067,891, filed on Oct. 12, 2020, now abandoned.

(60) Provisional application No. 62/915,065, filed on Oct. 15, 2019.

(51) Int. Cl.
*C07C 255/09* (2006.01)
*H01M 8/18* (2006.01)

(52) U.S. Cl.
CPC .......... *C07C 255/09* (2013.01); *H01M 8/188* (2013.01); *H01M 2300/0002* (2013.01)

(58) Field of Classification Search
CPC .................................................. C07C 255/09
See application file for complete search history.

(56) References Cited

PUBLICATIONS

Fukunaga, F. J. Am. Chem. Soc. 1976, 98, 610-611 (Year: 1976).*

* cited by examiner

*Primary Examiner* — Matthew P Coughlin
(74) *Attorney, Agent, or Firm* — J. Clinton Wimbish; Maynard Nexsen PC

(57) ABSTRACT

Hexasubstituted [3] radialene compounds are described herein. In some embodiments, the hexasubstituted [3] radialene compounds exhibit desirable water solubility and reversible redox activity in aqueous solutions, thereby facilitating employment of such compounds in aqueous redox flow batteries.

17 Claims, 8 Drawing Sheets

[3]radialene

*Unstable in air*

Tris(dialkylamino)-cyclopropenium

*Irreversible oxidation in water*

Hexacyano-[3]radialene dianion

*Reversible oxidation in water*

Asymmetric-[3]radialene dianion

*Enhanced solubility & performance*

Z2-Z3

2-3

1,4

1: $R_3$ = CN (%)

2: $R_1$ = CN, $R_2$ = $CO_2Me$ (%)

3: $R_1$ = $CO_2Me$; $R_2$ = CN (%)

4: $R_3$ = $CO_2Me$ (%)

| σ | | | | | |
|---|---|---|---|---|---|
| |  |  |  |  |  |
| σ | 0.36 | 0.45 | 0.50 | 0.54 | 0.57 |
| |  |  |  |  |  |
| σ | 0.66 | 0.72 | 0.80 | 0.96 | 0.96 |

HEXASUBSTITUTED RADIALENE COMPOUNDS AND APPLICATIONS THEREOF

RELATED APPLICATION DATA

The present application is a continuation-in-part pursuant to 35 U.S.C. § 120 of U.S. patent application Ser. No. 17/067,891 filed Oct. 12, 2020 which claims priority pursuant to 35 U.S.C. § 119(e) to U.S. Provisional patent application Ser. No. 62/915,065 filed Oct. 15, 2019.

FIELD

The present application relates to organic compounds for use in redox flow battery technologies and, in particular, to hexasubstituted radialene compounds as catholytes in aqueous radial flow batteries.

BACKGROUND

The need for efficient grid-scale energy storage has become crucial as the demand for renewables steadily increases. Redox flow battery (RFB) technologies have emerged as capable electrochemical energy storage devices to mediate the void between power generation and consumption. Conventional RFBs use inorganic materials as redox couples ($V_2O_5$, $Zn/Br_2$) and corrosive electrolytes such as sulfuric acid. Recently, aqueous organic RFBs consisting of light element-based active species have been shown to operate efficiently in laboratory scale devices. Aqueous soluble organic active species offer several advantages over traditional inorganic-based RFBs. Specifically, organic small molecules are earth-abundant compared to traditional vanadium-based active species and are therefore more favorable from an economic standpoint. Aqueous organic RFBs that operate at neutral pH are particularly attractive from a techno-economic and safety standpoint. Specifically, they are non-corrosive, environmentally friendly, and non-flammable. Additionally, they allow for the use of inexpensive electrolytes, such as NaCl, which can be coupled with low-cost ion-exchange membranes. It remains a challenge, however, to design soluble and stable organic active species for neutral pH aqueous RFBs.

SUMMARY

In view of the foregoing, hexasubstituted [3] radialene compounds are described herein. In some embodiments, the hexasubstituted [3] radialene compounds exhibit desirable water solubility and reversible redox activity in aqueous solutions, thereby facilitating employment of such compounds in aqueous redox flow batteries. In some embodiments, a hexasubstituted [3] radialene dianion is provided, wherein at least one substitution of the radialene dianion comprises a moiety selected from the group consisting of ester, amide, amine, polyalkylene oxide, alkylene glycol, sulfonate, hydroxyl, and heterocyclyl. In some embodiments, at least two substitutions of the hexasubstituted [3] radialene dianion comprise a moiety independently selected from the group consisting of ester, amide, amine, polyalkylene oxide, alkylene glycol, sulfonate, sulfonyl, hydroxyl, and heterocyclyl.

In another aspect, hexasubstituted [3] radialene dianions of Formula I are provided:

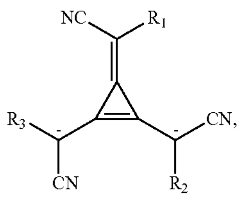

(I)

wherein $R_1$ is selected from the group consisting of —C(O)$OR_4$, —C(O)$NR_4R_5$, and heterocyclyl; and $R_2$ and $R_3$ are independently selected from the group consisting of cyano, —C(O)$OR_4$, —C(O)$NR_4R_5$, and heterocyclyl, wherein $R_4$ and $R_5$ are independently selected from the group consisting of hydrogen, alkyl, alcohol, glycol, amine, polyalkylene oxide, and sulfonate, wherein at least two of $R^1$-$R^3$ are the same.

In another aspect, hexasubstituted [3] radialene dianions of Formula II are provided:

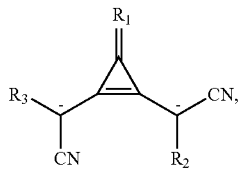

(II)

wherein $R_1$ is selected from the group consisting of cycloalkyl-dione, heterocycloalkyl-dione, cycloalkyl-trione, and heterocycloalkyl-trione, wherein the cycloalkyl-dione, heterocycloalkyl-dione, cycloalkyl-trione, and heterocycloalkyl-trione are optionally substituted with one or more substituents selected from the group consisting of alkyl and sulfanyl; and wherein $R_2$ and $R_3$ are independently selected from the group consisting of cyano, —C(O)$OR_4$, —C(O)$NR_4R_5$, and heterocyclyl, wherein $R_4$ and $R_5$ are independently selected from the group consisting of hydrogen, alkyl, alcohol, glycol, amine, polyalkylene oxide, and sulfonate.

Aqueous redox flow batteries are also described herein employing hexasubstituted [3] radialene dianions. In some embodiments, an aqueous redox flow battery comprises a hexasubstituted [3] radialene dianion catholyte, wherein at least one substitution of the radialene dianion comprises a moiety selected from the group consisting of ester, amide, amine, polyalkylene oxide, alkylene glycol, sulfonate, sulfonyl, hydroxyl, and heterocyclyl. Alternatively, an aqueous redox flow battery comprises a hexasubstituted [3] radialene dianion catholyte of Formula I and/or Formula II described above.

These and other embodiments are further described in the following detailed description.

DETAILED DESCRIPTION

Figure 1:
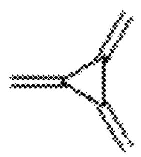
FIG. 1 presents examples of hexasubstituted [3] radialene dianions, according to some embodiments.
Figure 1:
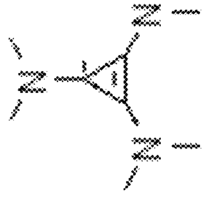
Figure 1:
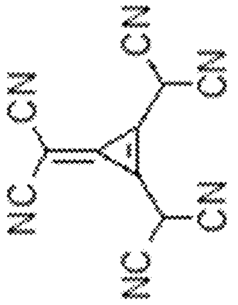
Figure 1:
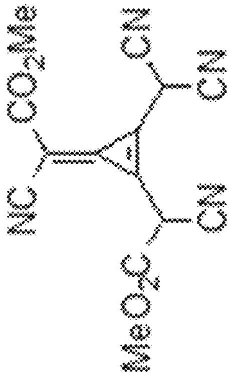

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$ or $C_1$-$C_{18}$.

The term "alkenyl" as used herein, alone or in combination, refers to a straight or branched chain hydrocarbon group having at least one carbon-carbon double bond and optionally substituted with one or more substituents The term "cycloalkyl" as used herein, alone or in combination, refers to a non-aromatic, mono- or multicyclic ring system optionally substituted with one or more ring substituents.

The term "heterocycloalkyl" as used herein, alone or in combination, refers to a non-aromatic, mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heterocyclyl" as used herein, alone or in combination, refers to a mono- or multicyclic ring system in which one or more of the atoms in the ring system is an element other than carbon, such as nitrogen, oxygen or sulfur, alone or in combination, and wherein the ring system is optionally substituted with one or more ring substituents. Heterocyclyl includes heterocycloalkyl and heteroaryl.

I. Hexasubstituted [3] Radialene Compounds

Hexasubstituted [3] radialene compounds are described herein. In some embodiments, the hexasubstituted [3] radialene compounds exhibit desirable water solubility and reversible redox activity in aqueous solutions, thereby facilitating employment of such compounds in aqueous redox flow batteries. In some embodiments, a hexasubstituted [3] radialene dianion is provided, wherein at least one substitution of the radialene dianion comprises a moiety selected from the group consisting of ester, amide, amine, polyalkylene oxide, alkylene glycol, sulfonate, sulfonyl, hydroxyl, and heterocyclyl. In some embodiments, at least two substitutions of the radialene dianion comprise a moiety independently selected from the group consisting of ester, amide, amine, polyalkylene oxide, alkylene glycol, sulfonate, sulfonyl, hydroxyl, and heterocyclyl. Moreover, in some embodiments, the at least two substitutions comprise the same moiety. As described herein, the balance of the substitutions of the hexasubstituted [3] radialene dianion can be cyano groups.

In another aspect, hexasubstituted [3] radialene dianions of Formula I are provided:

(I)

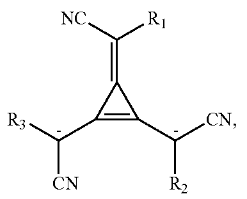

wherein $R_1$ is selected from the group consisting of —C(O)$OR_4$, —C(O)$NR_4R_5$, and heterocyclyl; and $R_2$ and $R_3$ are independently selected from the group consisting of cyano, —C(O)$OR_4$, —C(O)$NR_4R_5$, and heterocyclyl, wherein $R_4$ and $R_5$ are independently selected from the group consisting of hydrogen, alkyl, alcohol, glycol, amine, polyalkylene oxide, sulfonate, and sulfonyl, wherein at least two of $R^1$-$R^3$ are the same. In some embodiments, the heterocyclyl of any of $R_1$-$R_3$ can be heteroaryl. For example, in some embodiments, the heterocyclyl of any of $R_1$-$R_3$ is independently selected from the group consisting of imidazolium and pyridinium.

Figure 6:
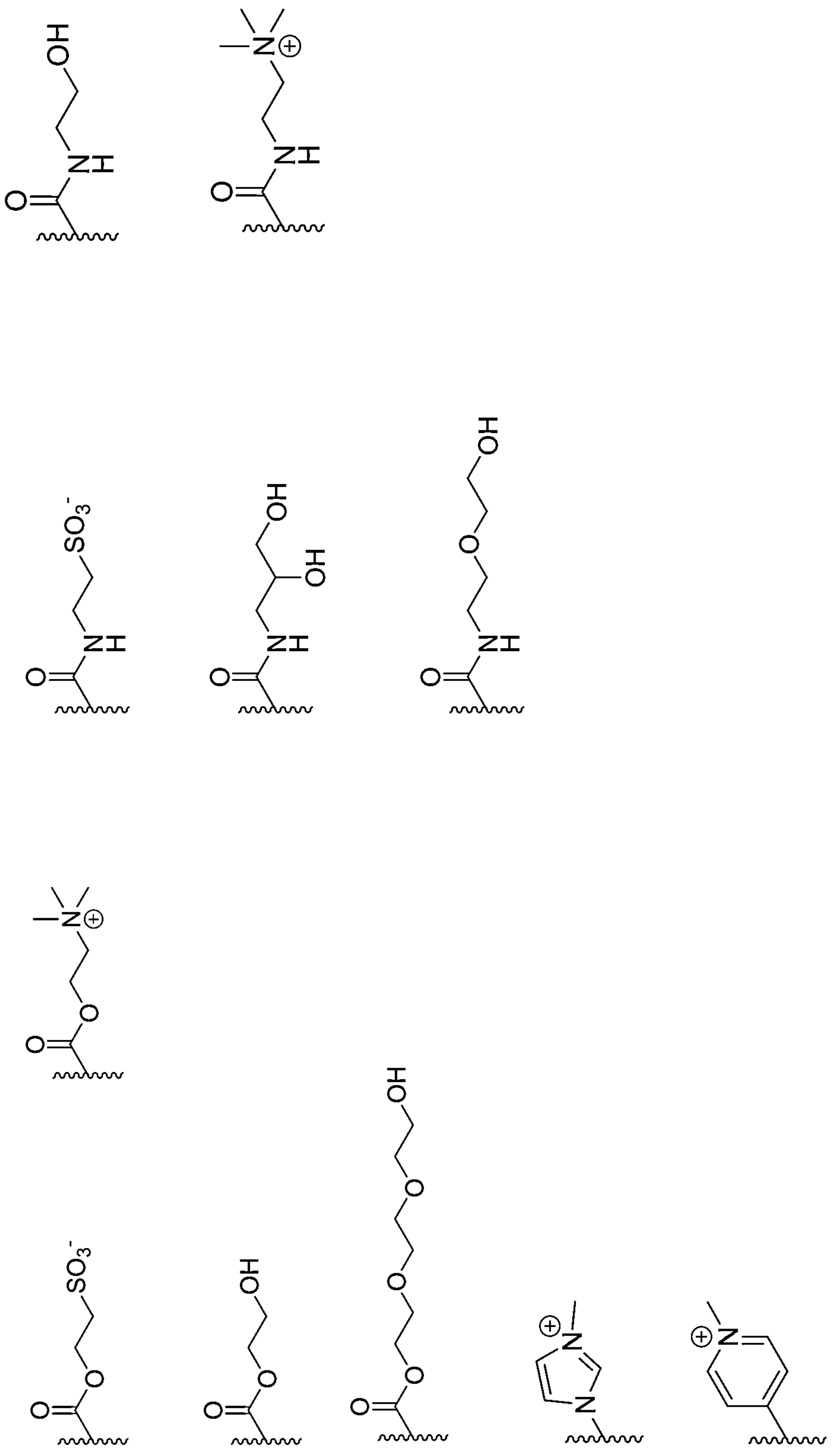
FIG. 6 provides various groups from which each $R_1$-$R_3$ can be independently selected according to some embodiments.

FIG. 6 provides various groups from which each $R_1$-$R_3$ can be independently selected according to some embodiments. Any combination of various groups of $R_1$-$R_3$ illustrated in FIG. 6 are contemplated herein. The various combinations can be selected according to several considerations including, but not limited to, solubility characteristics of the hexasubstituted [3] radialene dianion in water or aqueous environments, stability of the hexasubstituted [3] radialene dianion in air or aqueous solution, and/or reversible redox properties of the hexasubstituted [3] radialene dianion. The stability of hexasubstituted [3] radialene dianions described herein and their associated radical anion form is surprising since organic radicals are normally reactive toward aqueous environments. Additionally, as set forth in FIG. 6, groups from which $R_1$-$R_3$ can be independently selected include charged moieties, including quaternary amines and sulfonate groups.

Figure 8:
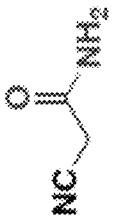
FIG. 8 illustrates various electron withdrawing groups that can be incorporated into hexasubstituted [3] radialene dianions described herein, according to some embodiments.
Figure 8:
Figure 8:
Figure 8:
Figure 8:
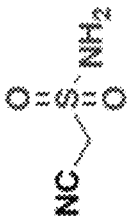
Figure 8:
Figure 8:
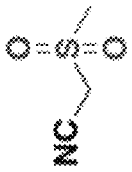
Figure 8:
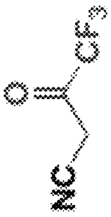
Figure 8:
Figure 8:

Additionally, in some embodiments, groups from which $R_1$-$R_3$ can be independently selected include electron withdrawing groups for voltage enhancements in redox flow battery applications. FIG. 8 illustrates various electron withdrawing groups that can be incorporated into hexasubstituted [3] radialene dianions described herein, according to the synthetic pathways illustrated in FIG. 3.

In another aspect, hexasubstituted [3] radialene dianions of Formula II are provided:

(II)

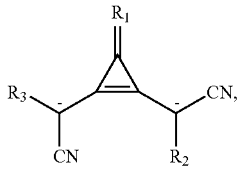

wherein $R_1$ is selected from the group consisting of cycloalkyl-dione, heterocycloalkyl-dione, cycloalkyl-trione, and heterocycloalkyl-trione, wherein the cycloalkyl-dione, heterocycloalkyl-dione, cycloalkyl-trione, and heterocycloalkyl-trione are optionally substituted with one or more substituents selected from the group consisting of alkyl and sulfanyl; and wherein $R_2$ and $R_3$ are independently selected from the group consisting of cyano, —C(O)$OR_4$, —C(O)$NR_4R_5$, and heterocyclyl, wherein $R_4$ and $R_5$ are independently selected from the group consisting of hydrogen, alkyl, alcohol, glycol, amine, polyalkylene oxide, and sulfonate.

In some embodiments, $R_1$ is of the formula:

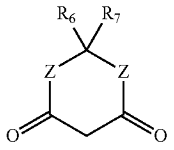

wherein $R_6$ and $R_7$ are independently selected from the group consisting of hydrogen, alkyl, and alkenyl, and Z is C, N, or O. In some embodiments, $R_6$ and $R_7$ are alkyl and Z is C. Alternatively, Z is O and $R_6$ and $R_7$ are alkyl.

Figure 7:
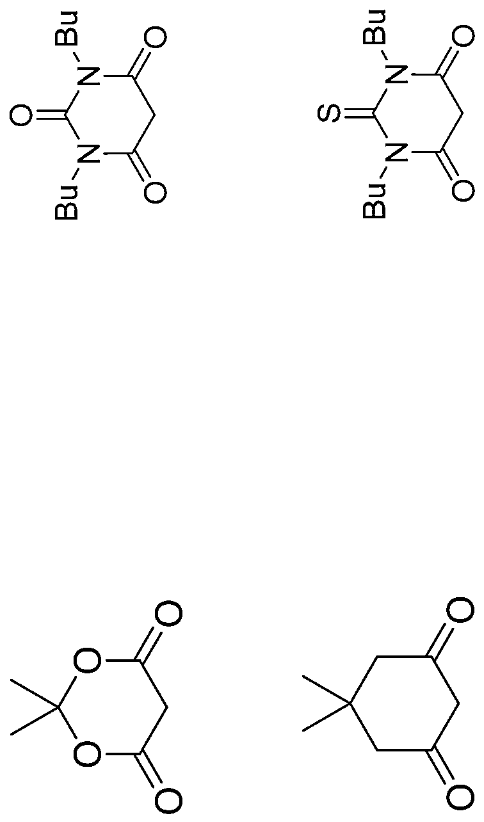
FIG. 7 provides various examples of hexasubstituted [3] radialene dianions of Formula II, according to some embodiments.

Moreover, in some embodiments, $R_1$ is of the formula:

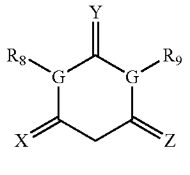

wherein $R_8$ and $R_9$ are independently selected from the group consisting of hydrogen, alkyl, and alkenyl, and wherein G is C or N, and wherein X, Y, and Z are independently selected from O and S. In some embodiments, G is N, and X, Y, and Z are each O. In other embodiments, G is N, Y is S, and X and Z are each O. FIG. 7 provides various examples of hexasubstituted [3] radialene dianions of Formula II, according to some embodiments.

In some embodiments, hexasubstituted [3] radialene dianions described and claimed herein can exhibit symmetric or asymmetric structure. Additionally, the radical anion form of hexasubstituted [3] radialene dianions described and claimed herein are also contemplated. As described further herein the hexasubstituted [3] radialene compounds exhibit reversible redox activity between the dianion and radical anion forms.

II. Redox Flow Batteries

Aqueous redox flow batteries are also described herein employing hexasubstituted [3] radialene dianions. In some embodiments, an aqueous redox flow battery comprises a hexasubstituted [3] radialene dianion catholyte, wherein at least one substitution of the radialene dianion comprises a moiety selected from the group consisting of ester, amide, amine, polyalkylene oxide, alkylene glycol, sulfonate, sulfonyl, hydroxyl, and heterocyclyl. Alternatively, an aqueous redox flow battery comprises a hexasubstituted [3] radialene dianion catholyte of Formula I and/or Formula II described in Section I above. Hexasubstituted [3] radialene dianions and their associated radical anion form can have any composition, structure, and/or properties described in Section I above. In some embodiments, aqueous solutions of hexasubstituted [3] radialene dianions are sufficiently conductive, thereby precluding the need for supporting electrolytes, such as NaCl and/or other salts.

In some embodiments, anolyte of aqueous redox flow batteries described herein comprise one or more organic compounds. For example, in one embodiment, the anolyte comprises 1,1'-bis(3-sulfonatopropyl)-4,4'-bipyridinium [$MV(SO_3)_2$]. Additionally, aqueous redox flow batteries described herein can exhibit neutral pH, thereby providing further environmentally friendly advantages.

These and other embodiments are further illustrated in the following non-limiting examples.

Example 1—Characterization of Hexacyano[3] Radialene for RFB Applications

Figure 3:
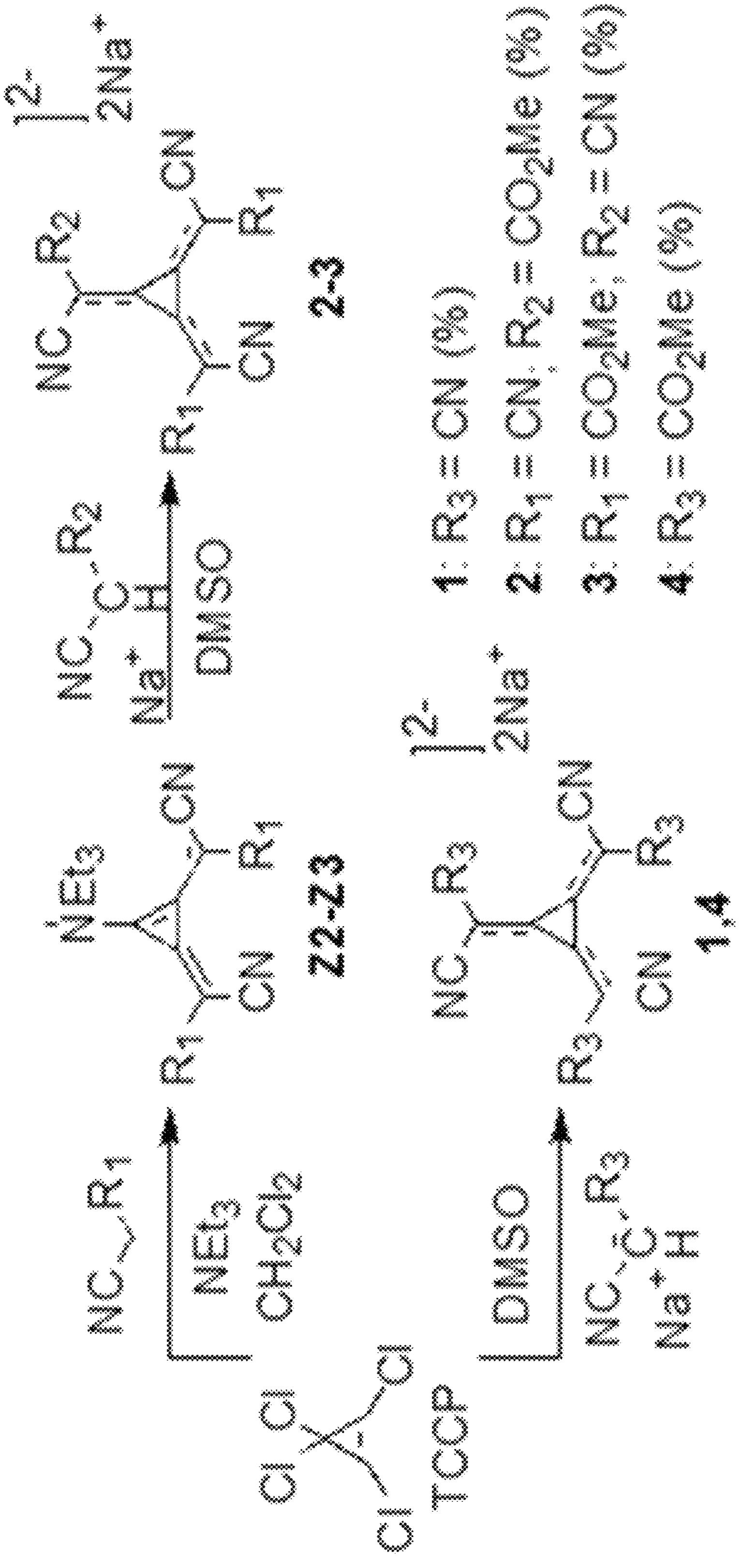
FIG. 3 illustrates synthetic routes for various hexasubstituted [3] radialene dianions described herein according to some embodiments.

Hexacyano[3] radialene ($Na_2C_6(CN)_6$), compound 1 in FIG. 3, was synthesized at low temperatures, on a large scale, and in high yield (for example 45 g, 91%). This convenient synthesis uses inexpensive precursors (tetrachlorocyclopropene (TCCP) and malononitrile), reagents (sodium hydride), and solvent (glyme). Hexacyano[3] radialene also exhibits modest solubility in water (25 mM), due to its dianionic nature. Furthermore, this compound is stable in air, and can be sequentially oxidized in two single-electron transfers. The product of the first oxidation, radical anion the compound ·- is particularly persistent. It can be isolated in high yield via chemical oxidation and stored in air indefinitely. Remarkably, the radical anion is thermally stable to above 180° C. The inherent stability of the compound and persistence of the radical anion ·- signifies that the redox couple is favorable for use in a RFB, a device in which long lifespan is required. Finally, aqueous solutions of the dianion are colorless, while the radical anion produces a deep blue color when dissolved. This is advantageous for visually following the charge-discharge characteristics of proposed RFBs.

Hexacyano[3] radialene was initially used as a model system to probe the efficacy of hexasubstituted [3] radialenes as redox couples in pH 7 aqueous solutions. A prerequisite for a practical aqueous catholyte is a high oxidation potential that occurs within the electrochemical window of water. The electrochemistry of $[C_6(CN)_6]^{2-}$ as a tetrabutylammonium (TBA) salt in organic solvents only. It was determined that both the dianion of the compound and radical anion of the compound ·- are stable and exhibit reversible redox activity in aqueous solutions at pH 7. Using cyclic voltammetry (CV), it was first established that the one electron oxidation of the dianion to the radical anion occurs at a potential favorable for use as a catholyte for RFBs, 480 mV. This oxidation potential is comparable to that of alkylammonium-functionalized ferrocene (410 mV) and 4-hydroxy-TEMPO (610 mV), two state-of the-art materials recently reported as catholyte components for neutral aqueous RFBs.

Plots of the square root of scan rate vs. peak current are linear within the ranges of 0-700 mV/s, which indicates that the redox couple is electrochemically reversible and diffusion-controlled are shown in the figures. From this data, the Randles-Sevcik equation was used to calculate the diffusion coefficient for the electron transfer process ($3.71\times10^{-6}$ $cm^2$/s). This value was almost identical to the diffusion coefficients of hydrophilic ferrocene derivatives in neutral pH solutions of NaCl. Additionally, solutions of both the dianion of the compound and radical anion of the compound ·- show no significant changes in peak current height when solutions are left to sit for five days (ESI). Such chemical stability is essential for durable RFB electrolytes.

Figure 2A:
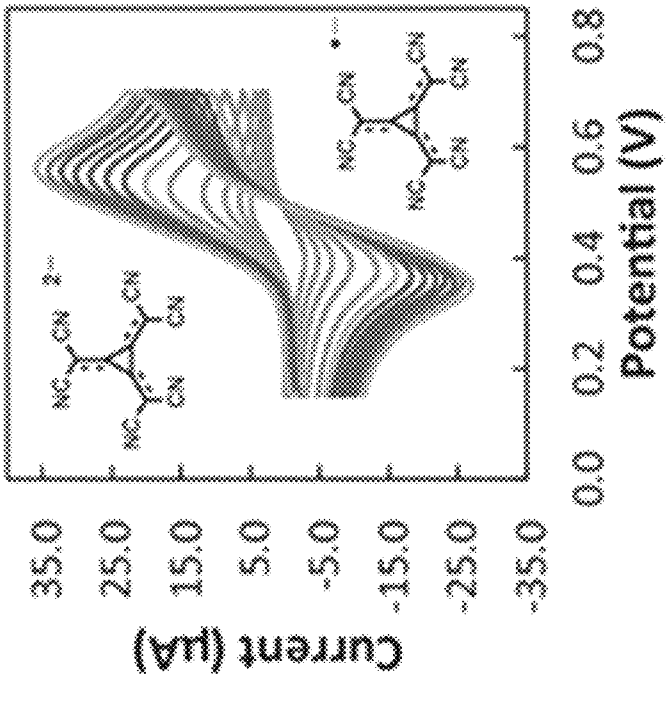
FIG. 2A provides cyclic voltammograms of a hexasubstituted [3] radialene dianion (1 mmol) using a glassy carbon (GC) working electrode, platinum auxiliary electrode, and Ag/AgCl reference electrode measured at various scan rates (10-700 mV/s) in water.
Figure 2B:
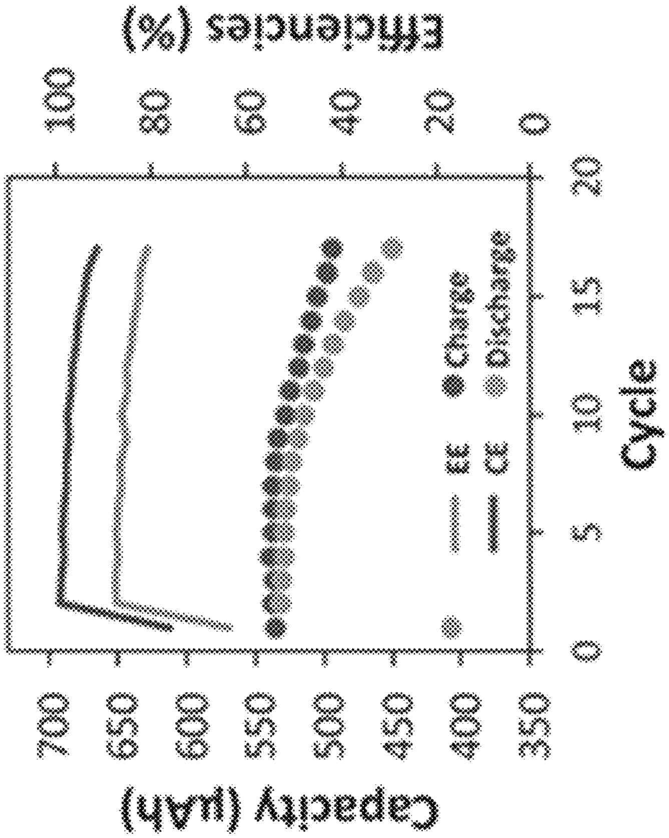
FIG. 2B provides a plot of capacity, coulombic efficiency (CE), and energy efficiency (EE) for the 1e-cycling experiment of an aqueous solution of a hexasubstituted [3] radialene dianion (10 mM) in an H cell.

The chemical reversibility of the redox couple in water was also investigated by performing preliminary galvanostatic charge-discharge measurements. The setup consisted of a symmetric static H-cell with 10 mM aqueous solutions of hexacyano[3] radialene, graphite felt working electrodes, and a Ag/AgCl reference electrode. A Selemion CSO cation-exchange membrane was used to separate the two components of the H-cell. This membrane allowed alkali cations to migrate efficiently and has recently been reported as a low-cost alternative to Nafion for neutral aqueous RFBs. Voltage cutoffs were set at 0.8 V and 0.15 V, respectively, to avoid generating the doubly oxidized, neutral, radialene that is unstable in air and insoluble in water. The desired couple exhibits 1e-charge-discharge cycling, with high energy and coulombic efficiencies (FIGS. 2A-2B).

Example 2—Asymmetric, Water Soluble Hexasubstituted [3] Radialenes

One nitrile group was systematically substituted at a time in an effort to preserve the favorable oxidation potential of the redox couple. To this end, a series of asymmetric, ester-substituted, [3] radialene species (FIG. 3, Compounds 1-4) were prepared via the zwitterionic synthetic method. The aqueous solubilities of these compounds in both the dianionic and radical anionic states were determined using UV/Vis spectroscopy (Table 1).

TABLE 1

Solubility and Electrochemical Properties of Compounds 1-4

| Property | 1 | 2 | 3 | 4 |
|---|---|---|---|---|
| Solubility | <0.1M | 0.19M | 0.45M | 0.82M |
| Radical Anion Solubility | <25 mM | 0.08M | 0.17M | <25 mM |
| Conductivity (mS/cm) | 13.2 (0.147) | 15.7 (2.36) | 36.7 (23.2) | 39 (0.23) |
| $E^{ox}_{1/2}$ | 0.48 V | 0.4 V | 0.35 V | 0.27 V |
| $i_{pc}/i_{pa}$ | 1.03 | 0.97 | 1.06 | 1.15 |

The mono-ester (2) was prepared and found that substituting one nitrile group with a methyl-ester unit improves the aqueous solubility by a factor of 10. Encouraged by this marked enhancement, the corresponding di- and tri-ester functionalized [3] radialenes (3 & 4) were synthesized for comparison. Increasing the number of methyl ester moieties resulted in higher solubility for the disodium salts (Table 1). Remarkably, the tri-ester disodium salt 3 exhibits a solubility of 0.85 M in water. These results demonstrate that even slight molecular modifications of the hexasubstituted [3] radialene scaffold drastically boosts aqueous solubility.

Density functional theory (DFT) calculations were performed to determine the spin density maps of compounds 1-4 as radical anions (ESI). Calculations indicate that the spin density is most prominently localized on the methyl ester alpha carbons in compounds 2-4. This was rationalized in terms of electron density: the more electron-rich cyanoester sites are easier to ionize than the malononitrile methylene, which is relatively electron-deficient in comparison. The spin density maps of compounds 4·- show the radical character to be distributed symmetrically, increasing the likelihood of dimerization interactions. These calculations support the observed low solubility of compound 4·- in water.

Figure 4A:
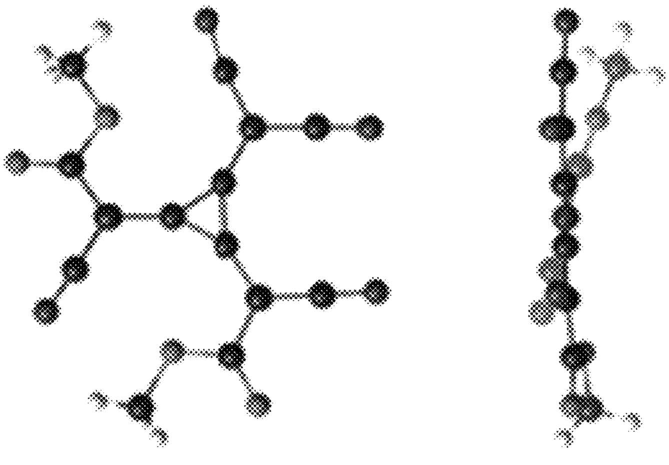
FIG. 4A illustrates top and side ball and stick diagrams of a diester-tetracyano [3] radialene dianion described herein.
Figure 4B:
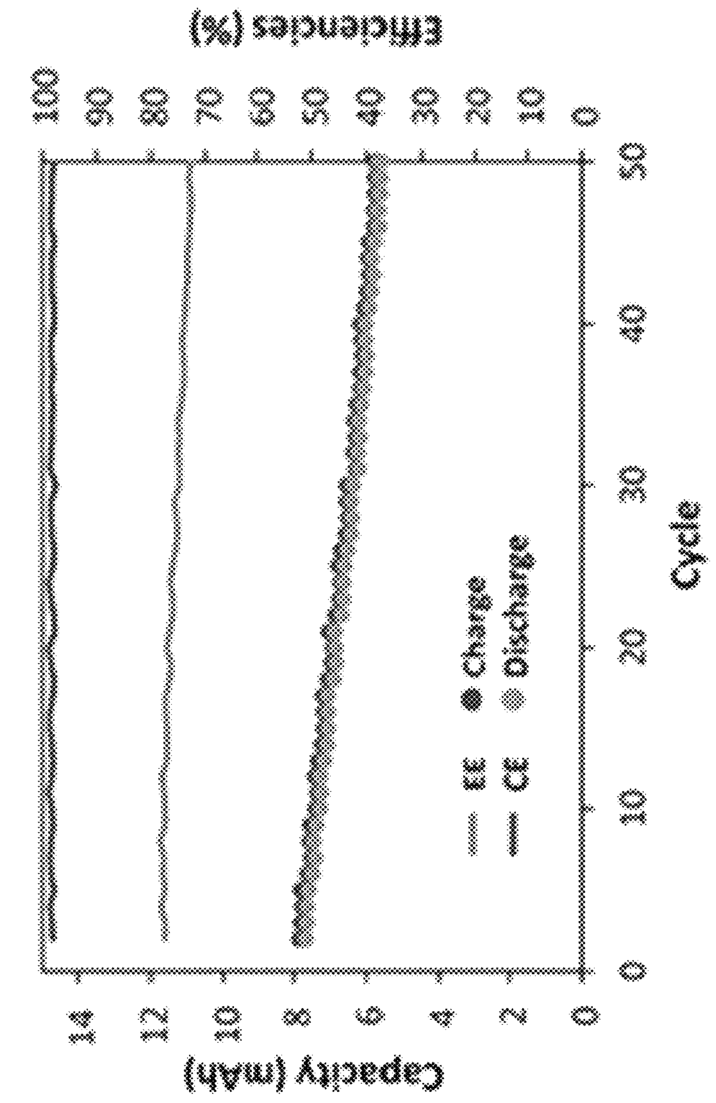
FIG. 4B provides a plot of capacity, coulombic efficiency, and energy efficiency for the 1e-cycling of the diester-tetracyano [3] radialene dianion of FIG. 4A.
Figure 5B:
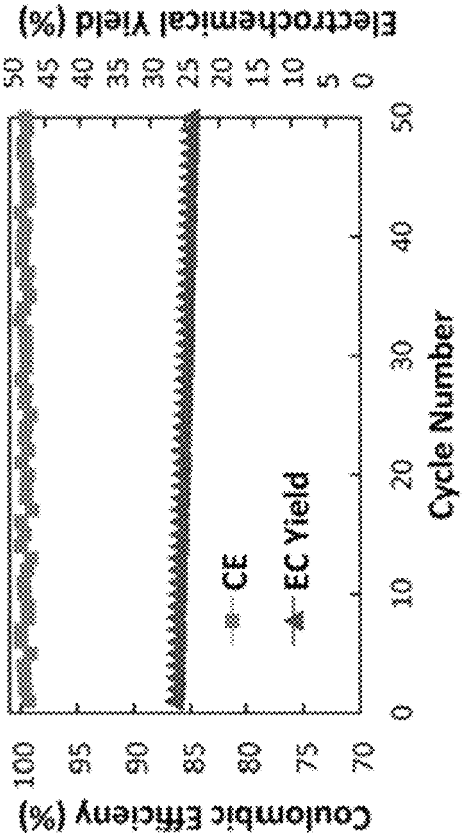
FIG. 5B characterizes the electrochemical yield and coulombic efficiency of a 0.1 M flow cell containing $MV(SO_2)_2$ and diester-tetracyano [3] radialene dianion over 50 cycles.
Figure 5A:
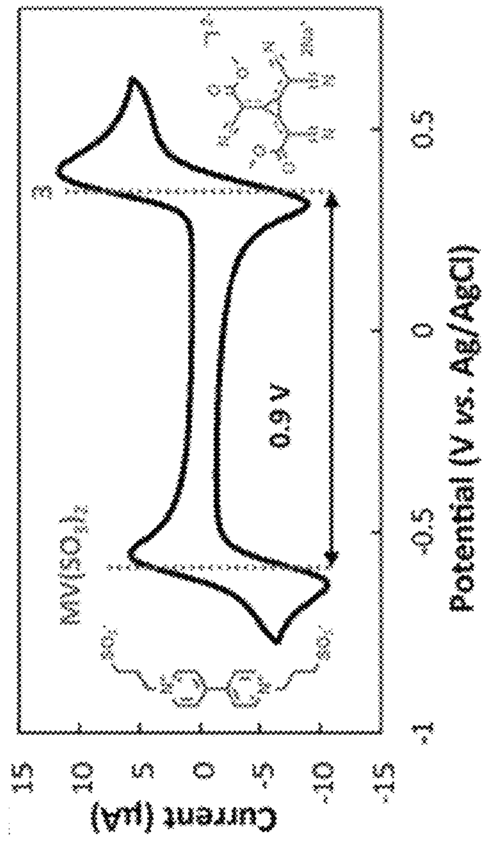
FIG. 5A provides a cyclic voltammogram of a mixture containing sulfonated-methyl viologen ($MV(SO_2)_2$, 1 mM) as the anolyte and diester-tetracyano [3] radialene dianion (1 mM) as the catholyte.

Diester compound 3 was selected for further analysis due to its favorable solubility in both redox states and its adequate oxidation potential in water. Electrochemical studies of compound 3 were performed to gauge its stability and galvanostatic cycling performance in aqueous solution. Cyclic voltammetry time studies over a period of five days reveal that the diester dianion of compound 3 is stable in water (ESI). This assuages concerns of the possibility of ester hydrolysis. Next, a symmetrical H-cell with a cation-exchange membrane separator was used for aqueous galvanostatic charge-discharge experiments (FIG. 4B). The compound 3 undergoes steady cycling over a period of 12 days (50 cycles). A high coulombic efficiency was observed (98.7%) and respectable energy efficiency (72%) after 50 cycles. Capacity retention in this H-cell experiment is also improved compared to the hexacyano[3] radialene-based electrolytes of Example 1. The higher relative capacity retention was ascribed to the asymmetry and non-planarity of the diester congener, which helps limit dimerization interactions. These results are particularly noteworthy considering the cycling studies on compound 3 were performed under higher concentration conditions that promote dimerization.

Crystals of the bis(tetrabutylammonium) (TBA) salt of 3 were also obtained and analyzed using single crystal X-ray diffraction. The structure clearly shows the asymmetry of the molecule and that the flexible methyl ester groups of compound 3 force the molecular surface to deviate from planarity (FIG. 4A). These features are expected to inhibit radical dimerization, which is hypothesized to lead to decreases in capacity.

Example 3—RFB Employing Hexasubstituted [3] Radialene Dianion Catholyte

A laboratory scale flow cell was constructed using the diester compound 3 as the catholyte and 1,1'-bis(3-sulfonatopropyl)-4,4'-bipyridinium [$MV(SO_3)_2$] as the anolyte. This anolyte was selected due to its ability to facilitate cation exchange with compound 3 during redox cycling and enables use of a low-cost Selemion cation exchange membrane. The cell had a theoretical operating voltage of 0.9 V and used a carbon-felt electrode (SGL GFD/5 $cm^2$ active area) with a serpentine flow field. The charge/discharge rate was set to 15 mA with a 2.5 mL/min flow rate. High coulombic efficiency (99.609%) was observed over a time period of 50 cycles. The electrochemical yield of the flow cell, which considers the experimental vs. theoretical capacity, was steady around 25%. This capacity was lower than expected. However, the low observed capacity fade over fifty cycles is noteworthy. A capacity loss of 0.046% per cycle was observed under these flow cell conditions. Additionally, it was observed that aqueous solutions of compound 3 were sufficiently conductive at 0.1 M, without the addition of NaCl supporting electrolytes, due to their inherent charge. This is advantageous for further lowering capital costs of future [3] radialene-based RFB implementation.

As described herein, hexasubstituted [3] radialene dianions are used for catholytes in neutral pH RFBs. The [3] radialene scaffold was found to be amenable to synthetic modifications that can increase its performance as a catholyte. Significant enhancements in aqueous solubility were obtained by desymmetrization via step-wise synthesis. Disruption of symmetry and planarity also led to improvements in aqueous galvanostatic cycling stability. A laboratory scale flow cell consisting of a diester-tetracyano [3] radialene catholyte coupled to a viologen anolyte showed steady cycling with high coulombic efficiency over 50 cycles. Remarkably, the dianionic nature of these active materials allows battery tests to be run in the absence of supporting electrolytes. Finally, the addition of hydrophilic functionalities may further increase the maximum solubility of these promising active species.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A hexasubstituted [3] radialene dianion of Formula II:

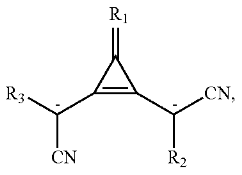

wherein $R_1$ is selected from the group consisting of cycloalkyl-dione, heterocycloalkyl-dione, cycloalkly-trione, and heterocycloalkyl-trione, wherein the cycloalkyl-dione, heterocycloalkyl-dione, cycloalkly-trione, and heterocycloalkyl-trione are optionally substituted with one or more substituents selected from the group consisting of alkyl and sulfanyl; and wherein $R_2$ and $R_3$ are independently selected from the group consisting of cyano, —C(O)$OR_4$, —C(O)$NR_4R_5$, and heterocyclyl, wherein $R_4$ and $R_5$ are independently selected from the group consisting of hydrogen, alkyl, alcohol, glycol, amine, polyalkylene oxide, and sulfonate.

2. The hexasubstituted [3] radialene dianion of claim 1, wherein the dianion is asymmetric.

3. A hexasubstituted [3] radialene dianion of Formula II:

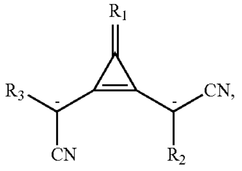

wherein $R_1$ is of the formula:

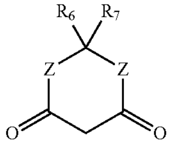

wherein $R_6$ and $R_7$ are independently selected from the group consisting of hydrogen, alkyl, and alkenyl, and Z is NH, $CH_2$, or O; and wherein $R_2$ and $R_3$ are independently selected from the group consisting of cyano, —C(O)$OR_4$, —C(O)$NR_4R_5$, and heterocyclyl, wherein $R_4$ and $R_5$ are independently selected from the group consisting of hydrogen, alkyl, alcohol, glycol, amine, polyalkylene oxide, and sulfonate.

4. The hexasubstituted [3] radialene dianion of claim 3, wherein Z is $CH_2$, and $R_6$ and $R_7$ are alkyl.

5. The hexasubstituted [3] radialene dianion of claim 3, wherein Z is O, and $R_6$ and $R_7$ are alkyl.

6. A hexasubstituted [3] radialene dianion of Formula II:

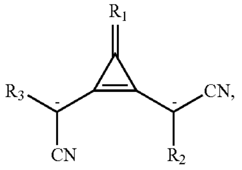

wherein $R_1$ is of the formula:

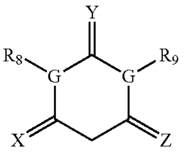

wherein $R_8$ and $R_9$ are independently selected from the group consisting of hydrogen, alkyl, and alkenyl, and wherein G is CH or N, and wherein X, Y, and Z are independently selected from O and S; and wherein $R_2$ and $R_3$ are independently selected from the group consisting of cyano, $C(O)OR_4$, $—C(O)NR_4R_5$, and heterocyclyl, wherein $R_4$ and $R_5$ are independently selected from the group consisting of hydrogen, alkyl, alcohol, glycol, amine, polyalkylene oxide, and sulfonate.

7. The hexasubstituted [3] radialene dianion of claim 6, wherein G is N, and X, Y, and Z are each O.

8. The hexasubstituted [3] radialene dianion of claim 6, wherein G is N, Y is S, and X and Z are each O.

9. An aqueous redox flow battery comprising:

a hexasubstituted [3] radialene dianion catholyte, wherein at least one substitution of the radialene dianion comprises a moiety selected from the group consisting of ester, amide, amine, alkylene oxide, alkylene glycol, sulfonate, hydroxyl, and heterocyclyl.

10. The aqueous redox flow battery of claim 9, wherein at least one substitution comprises a moiety selected from the group consisting of ester, amide, amine, alkylene oxide, alkylene glycol, sulfonate, hydroxyl, and heterocyclyl.

11. The aqueous redox flow batter of claim 10, wherein at least two substitutions of the hexasubstituted [3] radialene dianion catholyte comprise the same moiety.

12. The aqueous redox flow battery of claim 9, wherein the battery is neutral pH.

13. The aqueous redox flow battery of claim 9, wherein anolyte of the battery comprises an organic compound.

14. An aqueous redox flow battery comprising:

a hexasubstituted [3] radialene dianion catholyte of Formula I:

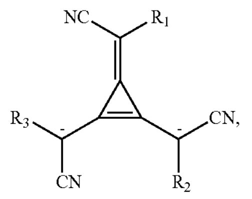

wherein $R_1$ is selected from the group consisting of $—C(O)OR_4$, $—C(O)NR_4R_5$, and heterocyclyl;

and $R_2$ and $R_3$ are independently selected from the group consisting of cyano, $—C(O)OR_4$, $—C(O)NR_4R_5$, and heterocyclyl, wherein $R_4$ and $R_5$ are independently selected from the group consisting of hydrogen, alkyl, alcohol, glycol, amine, polyalkylene oxide, and sulfonate, wherein at least two of $R^1$-$R^3$ are the same.

15. The aqueous redox flow batter of claim 14, wherein the radialene dianion is asymmetric.

16. The aqueous redox flow batter of claim 14, wherein each of $R^1$-$R^3$ are the same.

17. The aqueous redox flow battery of claim 14, wherein the battery is neutral pH.

* * * * *